US012597516B2

(12) United States Patent
Hsu

(10) Patent No.: US 12,597,516 B2
(45) Date of Patent: Apr. 7, 2026

(54) METHOD AND SYSTEM FOR CONTROLLING A PHYSICAL THERAPY DEVICE

(71) Applicant: Raymond Hsu, Shenzhen City (CN)

(72) Inventor: Raymond Hsu, Shenzhen City (CN)

( * ) Notice: Subject to any disclaimer, the term of this patent is extended or adjusted under 35 U.S.C. 154(b) by 311 days.

(21) Appl. No.: 18/357,961

(22) Filed: Jul. 24, 2023

(65) Prior Publication Data

US 2024/0304321 A1    Sep. 12, 2024

(51) Int. Cl.
| | |
|---|---|
| *G16H 40/67* | (2018.01) |
| *A61N 1/04* | (2006.01) |
| *A61N 1/36* | (2006.01) |
| *G16H 20/30* | (2018.01) |

(52) U.S. Cl.
CPC ........... *G16H 40/67* (2018.01); *A61N 1/0472* (2013.01); *A61N 1/3603* (2017.08); *G16H 20/30* (2018.01)

(58) Field of Classification Search
CPC ...... G16H 40/67; G16H 20/30; A61N 1/0472; A61N 1/3603; A61N 1/0452
See application file for complete search history.

(56) References Cited

U.S. PATENT DOCUMENTS

2014/0371814 A1* 12/2014 Spizzirri ............. A61N 1/0492
607/48
2020/0139106 A1* 5/2020 Chen ...................... A61N 1/403

\* cited by examiner

*Primary Examiner* — Ankit D Tejani
*Assistant Examiner* — Joshua Brendon Solomon
(74) *Attorney, Agent, or Firm* — Alexander Chen, Esq.

(57) ABSTRACT

The invention relates to the technical field of physiotherapy apparatuses, and discloses a method and system for controlling physiotherapy apparatuses. The method is applied to physiotherapy apparatuses. The physiotherapy apparatuses include a remote controller, a host and electrode sheets. The remote controller is wirelessly connected to the host computer. The remote controller is used to transmit signals to remotely control the host computer. The host computer and the electrode sheets are connected through connecting pieces, the connecting pieces are metal snap buttons, and the host computer is used to receive signals transmitted by the remote controller and generate pulse signals to be transmitted to the electrode sheets. The present invention connects a plurality of hosts through a remote controller, realizes wireless control of multiple hosts by a remote controller, and can use different massage modes for different parts to meet the needs of users for different massage modes. It also improves the reliability of product signal transmission by selecting a specific communication channel, and multiple hosts can receive control signals from the control terminal in a timely and accurate manner, reducing the interference of other signals on the equipment.

9 Claims, 4 Drawing Sheets

METHOD AND SYSTEM FOR CONTROLLING A PHYSICAL THERAPY DEVICE

TECHNICAL FIELD

The invention relates to the technical field of physical therapy instruments, in particular to a control method and system for physical therapy instruments.

BACKGROUND TECHNIQUE

Physiotherapy equipment generates electrical pulses to stimulate human muscle tissue and nerves to achieve the effects of relaxing muscles, relieving pain and even treating certain diseases. Most of the existing physiotherapy apparatuses combine the control host of the physiotherapy apparatus with electrodes for physiotherapy. By sticking the electrodes on the human body, pulse massage or treatment is performed. Generally, the electrode sheets and the control host of the physiotherapy instrument are connected through electrode wires, but for physiotherapy of different parts of the body, the length of the electrode wires required is different, which brings inconvenience to the user and affects the appearance.

The combination of wireless communication technology and physiotherapy apparatus makes the physiotherapy apparatus wireless. The control end of the physiotherapy apparatus is divided into two parts. One side is the remote control controlled by the user, which is used to control the intensity of the pulse and the transmission of the signal.

But the existing physical therapy instrument only allows one massage mode at a time, and does not consider the needs of different massage modes for different parts of the body. In addition, existing physiotherapy instruments usually use Bluetooth connection for wireless connection, but the transmission distance of Bluetooth is short, and the signal stability is poor, and multiple signal interferences are prone to occur during use, and there is also the problem of excessive energy consumption for data transmission. Therefore, a technique is needed to solve the above problems.

Contents of the Invention

Aiming at the problems raised in the background technology, the present invention provides a physical therapy device control method and system. By selecting a specific communication channel, the reliability of product signal transmission is improved, and different massage modes can be used for physiotherapy for different parts to meet the needs of users for different massage modes.

The present invention provides the following technical solutions: a method for controlling a physiotherapy apparatus, which is applied to a physiotherapy apparatus. The physiotherapy apparatus includes a remote controller, a host and electrode sheets, the remote controller is wirelessly connected to the host, and the remote controller is used to transmit signals to remotely control the host; the host is connected to the electrode via a connecting piece, the connecting piece is a metal snap button, and the host is used to receive signals transmitted by the remote controller and generate pulse signals to transmit to the electrode sheets;

The control method of the physical therapy instrument comprises the following steps:

S1. The remote controller randomly selects a channel as a fixed channel and sends a broadcast command;

S2. The host automatically polls all channels, sequentially sends frequency binding commands and waits for feedback from the remote controller, and if a broadcast command from the remote controller is received, the host switches to the corresponding channel and establishes a connection with the remote controller;

S3. The remote control obtains the parts to be stimulated corresponding to each host, and the user inputs the body parts stimulated by the host through the buttons of the remote control or voice input, and the body parts that can be selected by the remote control include shoulders, waist, joints, thighs and calves;

S4. According to the part to be stimulated, the remote controller acquires the recommended mode, recommended intensity and recommended time corresponding to the current part to be stimulated; the recommended mode, recommended intensity and recommended time are pre-set in the remote controller, and the techniques are respectively shaking, tapping, pinching, pulling, pinching, grasping, and lifting. The appropriate pulse width, pulse interval, duration, and intermittent time are combined to form a massage mode simulated by the basic treatment mode;

Preferably, before transmitting data packets corresponding to the recommended mode, recommended strength and recommended time to each host, the size S of the data packet is obtained, and the transmission rate v is adjusted according to the following formula:

$$v = \begin{cases} [0.1\alpha \cdot r_{max}, r_{max}] & S \geq M \\ S < M \end{cases}$$

$$\alpha = \exp(S - M)$$

Among them, rmax is the maximum transmission rate, which is the rate factor, M is the data packet threshold, and M depends on the peak value P and the average value A of the data packet generated by each use of the physiotherapy device within a period of time, $P = \{P_1, P_2, P_3, \ldots, P_n\}$, $A = \{A_1, A_2, A_3, \ldots, A_n\}$, the specific formula is:

$$M = \frac{\sum_{i=1}^{n} A_i}{n} + \frac{\sum_{i=1}^{n} P_i - \sum_{i=1}^{n} A_i}{3n}$$

n is the number of times the physical therapy device is used within a period of time.

Preferably, the specific steps for establishing a connection between the host and the remote controller in step S2 are:

S21. The host that receives the broadcast command broadcasts and feeds back the broadcast command and the host machine code of the remote controller, where the broadcast command includes the remote controller identification code and the serial number of the host;

S22. When the identification codes of the remote control are consistent, the serial number of the current host of the remote control has been connected;

S23. The remote controller sends the serial number of the host computer to establish a connection command;

S24. The remote controller issues a connection command;

S25, when the identification code of the remote control, the serial number of the main unit and the machine code of the main unit are consistent, the connection between the remote control and the main unit is successful.

Preferably, the remote controller is equipped with a display screen for displaying the stimulation site and the corresponding mode of the stimulation site. Before step S5, the display screen displays the recommended mode, recommended intensity and recommended time corresponding to the site to be stimulated. If the user accepts the recommended mode, recommended intensity and recommended time, perform step S5.

If the user does not accept the recommended mode, recommended intensity and recommended time, switch the mode of the corresponding site to be stimulated or change the time or intensity of the corresponding site to be stimulated by pressing the button or touch of the remote control, and set the updated mode, time or intensity corresponding to the site to be stimulated as the recommended mode, Recommend time or recommend intensity, and then execute step S5.

Preferably, the data packet includes host machine code, port number, mode parameter, time parameter and strength parameter, and the host receiving the data packet parses it to output a corresponding pulse signal.

Preferably, the mode parameters include pulse width, pulse interval, duration, off time. Preferably, the remote controller has a built-in voice recognition chip, which is used to recognize the instructions issued by the user, and send data packets to the corresponding hosts, or send data packets to all connected hosts if no execution host is specified.

Preferably, the remote control receives the user's voice wake-up command, and enters the wake-up state after the voice reply. After recognizing the command, the voice reply confirms, and sends a data packet to the host at the corresponding part. If the command is unclear, the remote control will inquire until the command is received. If no valid voice is received within 5s, the voice command is deemed to be abandoned.

Preferably, the voice command includes host mode switch, pause, time extension, increase and decrease intensity for corresponding parts and host mode switch, pause, extend time, increase and decrease intensity for all connections.

The present invention also provides the following technical solutions: a physical therapy instrument control system, the control system includes a wireless communication module, a storage module, a data processing module, a voice recognition module, and an output module;

The wireless communication module is used to wirelessly connect the remote controller with each host;

The storage module is used for storing wirelessly transmitted data packets;

The data processing module is used to obtain the size of the data packet, and adjust the transmission rate;

The speech recognition module is used to recognize the instructions issued by the user; The output module is used to analyze the data packet to output the corresponding pulse signal.

The present invention has the following beneficial effects:

In the present invention, one remote controller is connected with multiple hosts to realize wireless control of multiple hosts by one remote controller, and different massage modes can be used for different parts, which simplifies the user's operation; when the user uses the recommended mode for the first time, there is no need to manually set the physiotherapy parameters of the physiotherapy device, which improves the intelligence of the physiotherapy device and improves the user experience; by selecting a specific communication channel, the reliability of product signal transmission is improved, and multiple hosts can receive control signals from the control terminal in a timely and accurate manner, reducing the interference of other signals to the equipment; The transmission rate can effectively reduce the energy consumption of wireless transmission and reduce the delay of complex instructions.

Detailed Ways

The following will clearly and completely describe the technical solutions in the embodiments of the present invention with reference to the accompanying drawings in the embodiments of the present invention. Obviously, the described embodiments are only some of the embodiments of the present invention, not all of them. Based on the embodiments of the present invention, all other embodiments obtained by persons of ordinary skill in the art without making creative efforts belong to the protection scope of the present invention.

Figure 1:
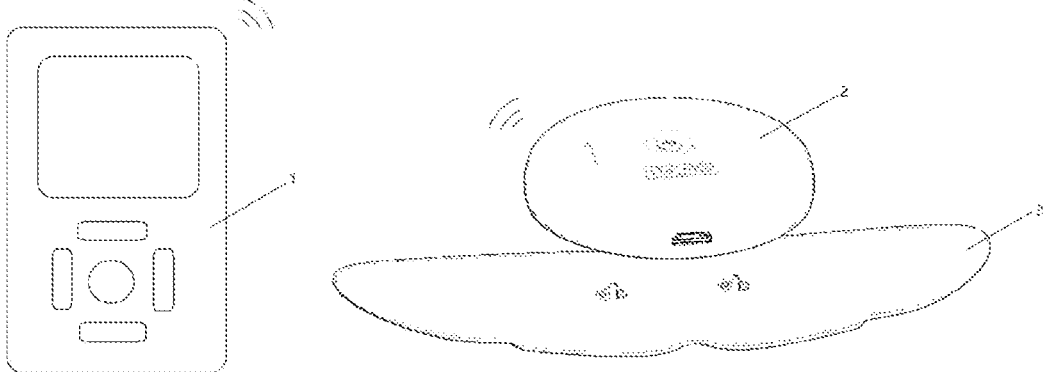
FIG. 1 is the structural diagram of physiotherapy instrument device of the present invention.

Please refer to FIG. 1, in a kind of preferred embodiment, a kind of physiotherapist control method is applied to physiotherapist, and described physiotherapist comprises remote controller 1, main frame 2 and electrode sheet 3, and described remote controller 1 is connected wirelessly with described host computer 2, and described remote controller 1 is used for transmitting signal remote control described host computer 2;

The control method of the physical therapy instrument comprises the following steps: When the user needs 3 hosts for massage, take out the host with the first 3 logos and turn it on, and input the number of hosts used after the remote control is turned on.

S1. The remote controller is connected to the host using 2.4G wireless communication, and the following three channels are used by default: 2416, 2432, and 2464; the remote controller randomly selects a channel as a fixed channel and sends a broadcast command.

Figure 2:
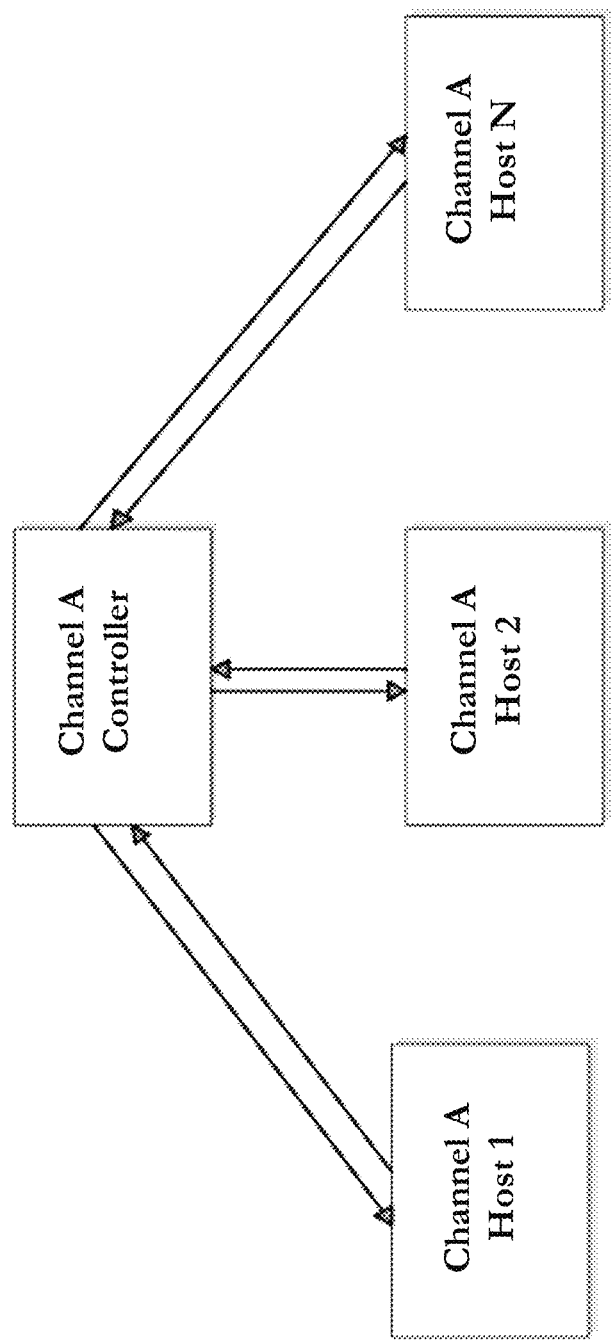
FIG. 2 is the frequency pairing structural diagram of the remote controller and the host computer of the present invention.
Figure 3:
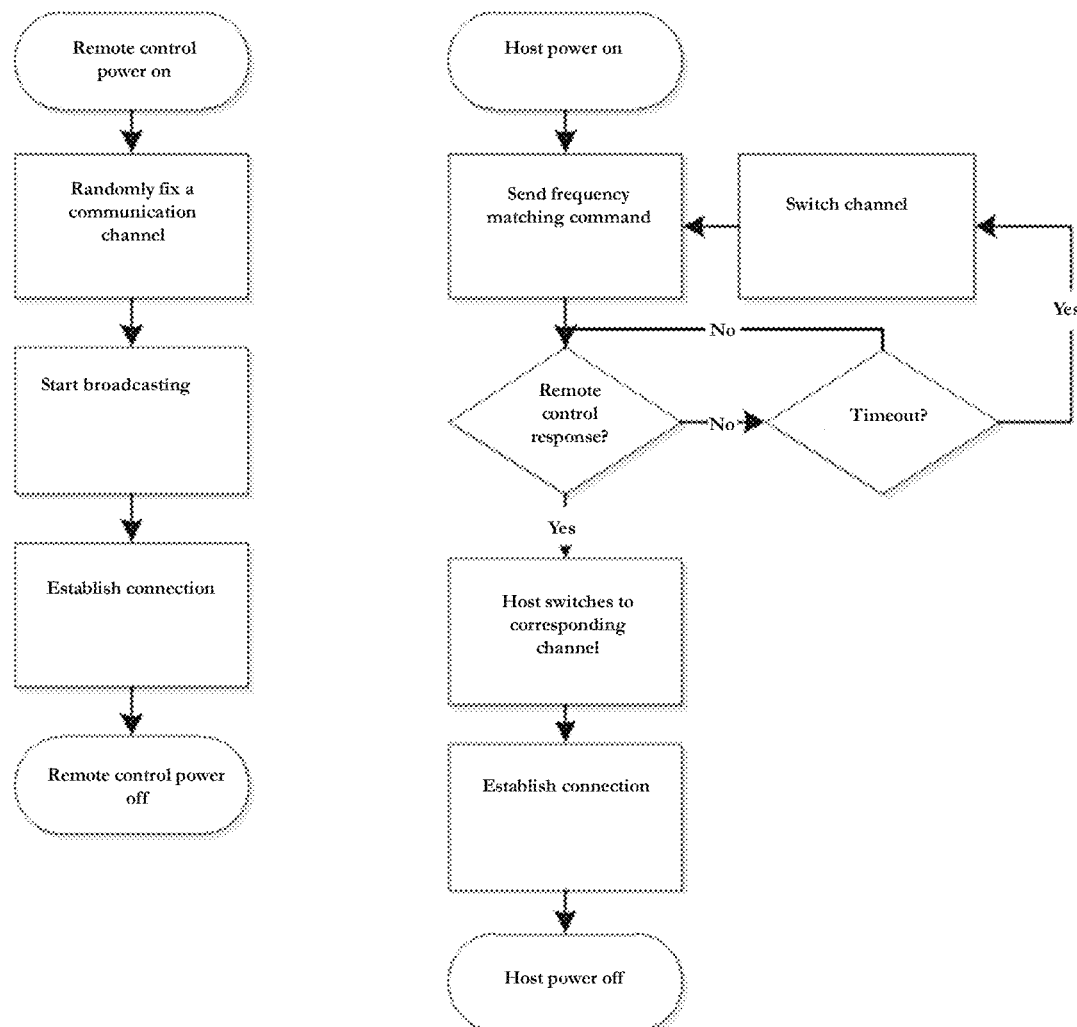
FIG. 3 is the flow chart of the frequency binding between the remote controller and the host of the present invention.

S2. As shown in FIGS. 2 and 3, the host automatically polls all channels, and sequentially sends frequency binding commands to wait for feedback from the remote controller. If a broadcast command from the remote controller is received, the host switches to the corresponding channel and establishes a connection with the remote controller.

S3. The remote control acquires the parts to be stimulated corresponding to each host, and the user inputs the body parts to be stimulated by the host through the buttons of the remote control or voice input. The body parts available for the remote control include shoulders, waist, joints, thighs and calves.

Beneficially, the specific steps for the above-mentioned remote controller to obtain the parts to be stimulated corresponding to each host are as follows: after the host is connected to the remote controller, it vibrates sequentially according to the serial number of the host. During the vibration of the host, the user inputs the corresponding site to be stimulated by the button of the remote controller or voice input. After the user inputs the confirmation command, the host stops vibrating, and the next host starts to vibrate until the remote controller obtains the corresponding parts to be stimulated of all hosts;

Beneficially, the above-mentioned method for the user to input the part to be stimulated corresponding to the main unit by voice is for example: after the main unit is connected to the remote controller, it will vibrate sequentially according to the serial number of the main unit. For example, when the main unit located on the left shoulder is vibrating, the user will say "left shoulder" to the remote control, and after inputting a confirmation command, the main unit will stop vibrating, and the next main unit will start to vibrate until the corresponding relationship between all main units and the parts to be stimulated is obtained.

Beneficially, the host sends out vibration to remind the user of the body part where the host is located, which simplifies the user's operation and improves the user's experience. S4. According to the part to be stimulated, the remote control obtains the recommended mode, recommended intensity and recommended time corresponding to the current part to be stimulated; the recommended mode, recommended intensity and recommended time are pre-set in the remote control, as shown in Table 1 below.

TABLE 1

| Mode Number | Pulse Width (μs) | Pulse Interval (ms) | Duration (s) | Off Time (s) |
|---|---|---|---|---|
| Shake | 260 | 100 | 5.6 | 2.3 |
| Knock | 260 | 320 | 连续 | 0 |
| Pinch | 200 | 10 | 6 | 2.2 |
| Pull | 400 | 5 | 5.8 | 2.2 |
| Pinch | 200 | 2 | 5.8 | 2.2 |
| Grasp | 100 | 1 | 5.8 | 2.2 |
| Tina | 100 | 0.3 | 5.8 | 2.2 |

In this embodiment, before transmitting data packets corresponding to the recommended mode, recommended strength and recommended time to each host, the size S of the data packet is obtained, and the transmission rate v is adjusted according to the following formula:

$$v = \begin{cases} [0.1\alpha \cdot r_{max}, r_{max}] & S \geq M \\ & S < M \end{cases}$$

$$\alpha = \exp(S - M)$$

Among them, $r_{max}$ is the maximum transmission rate, which is the rate factor, M is the data packet threshold, and M depends on the peak value P and the average value A of the data packet generated by each use of the physiotherapy device within a period of time, $P=\{P_1, P_2, P_3, \ldots, P_n\}$, $A=\{A_1, A_2, A_3, \ldots, A_n\}$, the specific formula is:

$$M = \frac{\sum_{i=1}^{n} A_i}{n} + \frac{\sum_{i=1}^{n} P_i - \sum_{i=1}^{n} A_i}{3n}$$

n is the number of times the physiotherapy device is used within a period of time. For example, the 4 physiotherapy devices used in the previous month produced 4 peaks and 4 average values. Based on this data, the data packet threshold M is calculated. When the physiotherapy device is used in the current month, each time the data is transmitted, if the data packet size is greater than M, it will be transmitted at the rate, otherwise, it will be transmitted at the rate.

Figure 4:
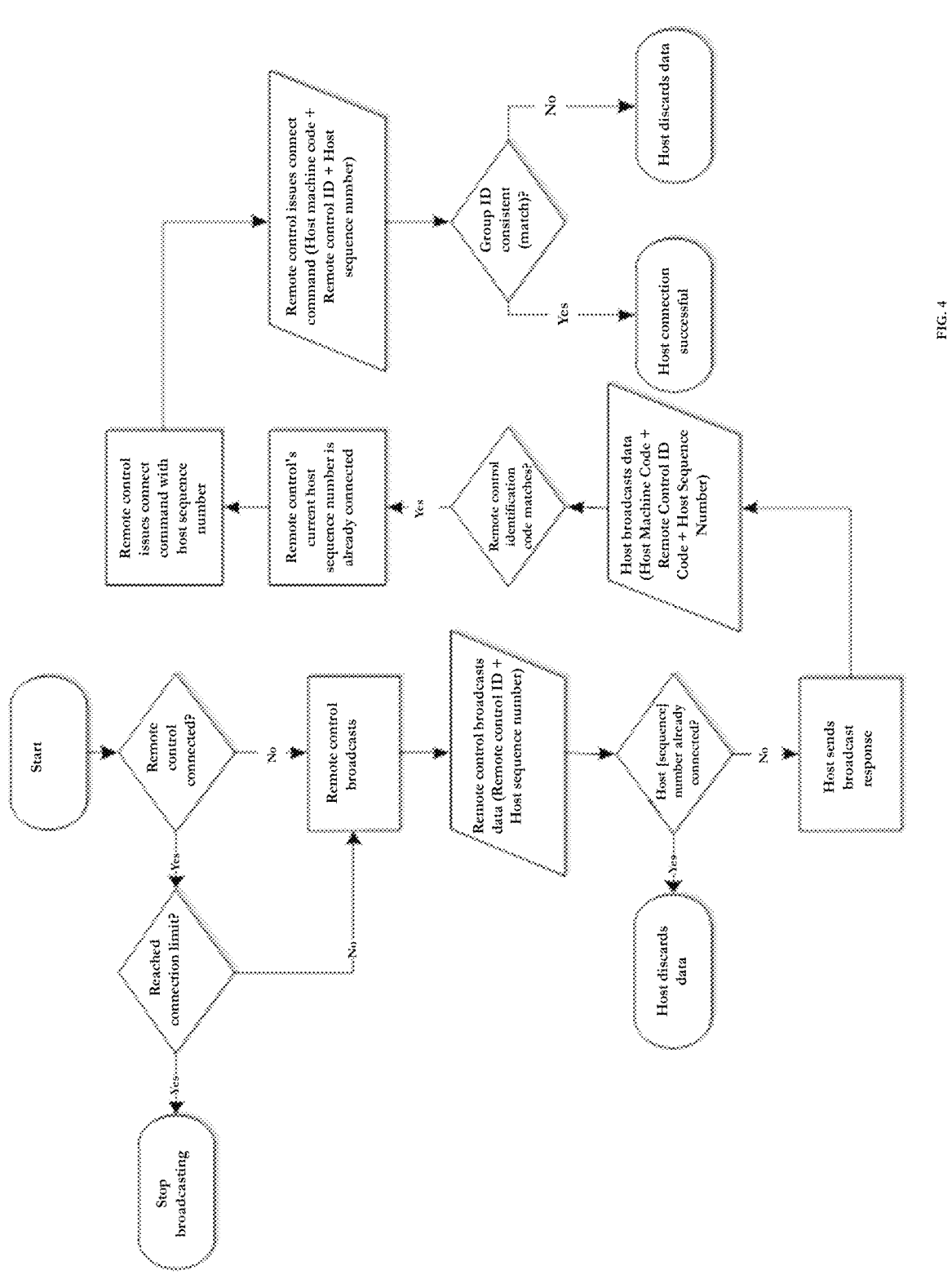
FIG. 4 is the connection flowchart of remote controller and host computer of the present invention, Among them, 1 is the remote control, 2 is the host, and 3 is the electrode sheet.

In this embodiment, as shown in FIG. 4, the specific steps for establishing a connection between the host and the remote controller in step S2 are: for example, the peak value and average value of the data packets generated by each use of the physical therapy device in the previous month, S21. The host that receives the broadcast command broadcasts and feeds back the broadcast command and the host machine code of the remote controller, where the broadcast command includes the remote controller identification code and the serial number of the host;

S22. When the identification codes of the remote control are consistent, the serial number of the current host of the remote control has been connected;

S23. The remote controller sends the serial number of the host computer to establish a connection command;

S24. The remote controller issues a connection command;

S25, when the identification code of the remote control, the serial number of the main unit and the machine code of the main unit are consistent, the connection between the remote control and the main unit is successful.

In step S21, the remote controller has received the broadcast feedback from the host. In step S22, the remote controller thinks that the host with this serial number has been connected to the remote controller. In steps S23 and S24, the host confirms the connection with the remote controller.

In this embodiment, the remote controller is equipped with a display screen for displaying the corresponding mode of the stimulation part and the stimulation part. Before step S5, the display screen displays the recommended mode, recommended strength and recommended time corresponding to the part to be stimulated. The updated mode, time or intensity corresponding to the stimulation site is set as the recommended mode, recommended time or recommended intensity, and then step S5 is executed.

In this embodiment, the data packet includes a host machine code, a port number, a mode parameter, a time parameter, and an intensity parameter, and the host receiving the data packet parses it to output a corresponding pulse signal.

In this embodiment, the mode parameters include pulse width, pulse interval, duration, and off time.

In this embodiment, the remote controller has a built-in voice recognition chip, which is used to recognize the instructions issued by the user, and send data packets to the corresponding hosts. If no execution host is specified, send data packets to all connected hosts.

In this embodiment, the remote control receives the user's voice wake-up command, and enters the wake-up state after the voice reply. After recognizing the command, the voice reply confirms, and sends a data packet to the host at the corresponding part.

In a preferred embodiment, the user issues an instruction: pinch the waist, and the remote controller voice replies: OK, the remote controller identifies the host corresponding to the waist, and the host establishes a data connection and then sends a data packet. The data packet includes the mode parameters of the pinch mode, and the waist mode is updated on the display screen.

In this embodiment, the voice command includes host mode switch, pause, time extension, increase and decrease intensity for corresponding parts and host mode switch, pause, extend time, increase and decrease intensity for all connections.

In a preferred embodiment, a physiotherapy instrument control system, the control system includes a wireless communication module, a storage module, a data processing module, a voice recognition module, and an output module;

The wireless communication module is used to wirelessly connect the remote controller with each host;

The storage module is used for storing wirelessly transmitted data packets;

The data processing module is used to obtain the size of the data packet, and adjust the transmission rate;

The speech recognition module is used to recognize the instructions issued by the user; The output module is used to analyze the data packet to output the corresponding pulse signal.

Although the embodiment of the present invention has been shown and described, for those of ordinary skill in the art, it can be understood that various changes, modifications, replacements and modifications can be made to these embodiments without departing from the principle and spirit of the present invention, and the scope of the present invention is defined by the appended claims and their equivalents.

The invention claimed is:

1. A method for controlling a physical therapy device, applied to a physical therapy device comprising a remote controller, a host, and electrode sheets; wherein the remote controller is wirelessly connected to the host and configured to transmit signals to remotely control the host; wherein the host is connected to the electrode sheets through a connecting member that is a metal snap button; and wherein the host is configured to receive signals transmitted by the remote controller and generate a pulse signal that is transmitted to the electrode sheets; wherein the method comprises the following steps:

Step 1, comprising the remote controller randomly selecting a channel as a fixed channel and sending a broadcast command;

Step 2, comprising the host automatically polling all channels, sequentially sending frequency binding commands and waiting for feedback from the remote controller, and if the broadcast command from the remote controller is received, switching to the corresponding channel and stablishing a connection with the remote controller;

Step 3, comprising the remote controller obtaining parts to be stimulated corresponding to each host;

Step 4. comprising, according to each part to be stimulated, the remote controller obtaining a recommended mode, recommended intensity and recommended time corresponding to the current part to be stimulated; and Step 5. comprising the remote controller establishing a data transmission connection with each host based on multi-thread processing, and transmitting data packets corresponding to the recommended mode, recommended intensity, and recommended time to each host.

2. The method of claim 1, wherein, before transmitting the data packets corresponding to the recommended mode, recommended strength and recommended time to each host, the size S of the data packet is obtained, and the transmission rate v is adjusted according to the following formula:

$$
v = \begin{cases} [0.1\alpha \cdot r_{max}, r_{max}] & S \geq M \\ S < M \end{cases}
$$
$$
\alpha = \exp(S - M)
$$

Among them, rmax is the maximum transmission rate, which is the rate factor, M is the data packet threshold, and M depends on the peak value P and the average value A of the data packet generated by each use of the physiotherapy device within a period of time, $P=\{P_1, P_2, P_3, \ldots, P_n\}$, $A=\{A_1, A_2, A_3, \ldots, A_n\}$, the specific formula is:

$$
M = \frac{\sum_{i=1}^{n} A_i}{n} + \frac{\sum_{i=1}^{n} P_i - \sum_{i=1}^{n} A_i}{3n}
$$

n is the number of times the physical therapy device is used within a period of time.

3. The method of claim 1, wherein the specific steps for establishing a connection between the host and the remote controller in step S2 are as follows:

S21. The host that receives the broadcast command broadcasts and feeds back the broadcast command and the host machine code of the remote controller, where the broadcast command includes the remote controller identification code and the serial number of the host;

S22. When the identification codes of the remote controllers are the same, the current host serial number of the remote controllers has been connected;

S23. The remote controller sends the serial number of the host computer to establish a connection command;

S24. The remote controller issues a connection command;

S25, when the identification code of the remote control, the serial number of the main unit and the machine code of the main unit are consistent, the connection between the remote control and the main unit is successful.

4. The method of claim 1, characterized in that the remote controller is equipped with a display screen for displaying the stimulation site and the corresponding mode of the stimulation site;

Before step S5, the display screen displays the recommended mode, recommended intensity and recommended time corresponding to the site to be stimulated;

If the user accepts the recommended mode, recommended intensity and recommended time, step S5 is performed;

If the user does not accept the recommended mode, recommended intensity and recommended time, switch the mode of the corresponding site to be stimulated or change the time or intensity of the corresponding site to be stimulated by pressing the button or touch of the remote control;

The updated mode, time or intensity corresponding to the part is set as the recommended mode, recommended time or recommended intensity, and then step S5 is executed.

5. The method of claim 1, wherein the data packet includes host machine code, port number, mode parameter, time parameter, and intensity parameter, and the host computer that receives the data packet parses it to output a corresponding pulse signal.

6. The method of claim 5, wherein the mode parameters include pulse width, pulse interval, duration, and off time.

7. The method of claim 1, wherein the remote controller has a built-in speech recognition chip for recognizing instructions issued by the user, and sending data packets to the corresponding hosts, and sending data packets to all connected hosts if no execution host is specified.

8. The method of claim 7, wherein the remote controller receives the voice wake-up command from the user, and enters the wake-up state after the voice reply, and confirms the voice reply after recognizing the command, and sends a data packet to the host at the corresponding part, if the command is unclear, the remote controller will inquire until the command is received, and if no valid voice is received within 5 s, the voice command is deemed to be abandoned.

9. The method of claim 8, wherein the voice command includes host mode switching, pause, time extension, addition and subtraction intensity for corresponding parts, and host mode switching, pause, extension time, addition and subtraction intensity for all connections.

* * * * *